United States Patent [19]

Dick et al.

[11] Patent Number: 5,244,906
[45] Date of Patent: Sep. 14, 1993

[54] INSECT CONTROL WITH SUBSTITUTED OXADIAZOLE AND THIADIAZOLE COMPOUNDS

[75] Inventors: Michael R. Dick, Concord; Chi-Ping Chang, Walnut Creek; James E. Dripps, Concord; Susan Wollowitz, Walnut Creek, all of Calif.

[73] Assignee: DowElanco, Indianapolis, Ind.

[21] Appl. No.: 824,658

[22] Filed: Jan. 23, 1992

[51] Int. Cl.$^5$ .................... A01N 43/40; A01N 43/42; A01N 43/82; A01N 43/90

[52] U.S. Cl. .................................. 514/299; 514/305; 514/326; 514/340; 514/342; 514/361; 514/363; 514/364

[58] Field of Search .............. 514/299, 305, 326, 340, 514/342, 361, 363, 364

[56] References Cited

U.S. PATENT DOCUMENTS

| | | | |
|---|---|---|---|
| 4,722,934 | 2/1988 | Matsumoto et al. | 514/363 |
| 4,870,073 | 9/1989 | Wätjen et al. | 514/214 |
| 4,943,584 | 7/1990 | Theobald et al. | 514/380 |
| 4,952,587 | 8/1990 | Baker et al. | 514/305 |
| 5,134,146 | 7/1992 | Showell et al. | 514/299 |

FOREIGN PATENT DOCUMENTS

| | | |
|---|---|---|
| 0239309 | 9/1987 | European Pat. Off. |
| 0257741 | 3/1988 | European Pat. Off. |
| 0323864 | 7/1989 | European Pat. Off. |

OTHER PUBLICATIONS

Bigg et al., Nature 262, 220–222 (1976).
Street et al., J. Med. Chem., 33, 2690–2697 (1990).
Saunders et al., J. Chem. Soc. Chem. Commun., 1618–1619 (1988).
Saunders et al., J. Med. Chem., 33, 1128–1138 (1990).
Showell et al., J. Med. Chem., 34, 1086–1094 (1991).
MacLeod et al., J. Med. Chem., 33, 2052–2059 (1990).
Sauerberg et al., J. Med. Chem., 34, 687–692 (1991).
Corronc et al., Pesticide Science, 33, 205–211 (1991).

Primary Examiner—Allen J. Robinson
Attorney, Agent, or Firm—D. Wendell Osborne

[57] ABSTRACT

Insects, especially sucking insects, such as brown planthoppers, and phytophageous mites, such as two-spotted spider mites, are controlled by applying an oxadiazole or thiadiazole compound substituted on a carbon atom by an aliphatic nitrogen heterocyclic moiety composed of at least one five or six membered ring. The compound 3-(3-amino-1,2,4-oxadiazol-5-yl)-1-azabicyclo[2,2,2]octane is typical.

11 Claims, No Drawings

INSECT CONTROL WITH SUBSTITUTED OXADIAZOLE AND THIADIAZOLE COMPOUNDS

BACKGROUND OF THE INVENTION

The present invention relates to a method of controlling insects and arachnids by treatment with insecticidal heterocyclic compounds and to insecticidal compositions useful in the method.

The control of insects and arachnids is critical to modern agriculture and to the maintenance of public health. Although many organic compounds are known to be toxic to insects and methods of killing and controlling insects based on them are known, different organic compounds that are more efficacious, are less toxic to mammals, are more compatible with the environment, are not cross-resistant with established insecticides, are less expensive, or have other new or improved properties are constantly sought and when found are highly valued.

A few oxadiazole and thiadiazole ring containing compounds, such as the oxadiazolyl substituted imidazobenzazepine compounds disclosed in U.S. Pat. No. 4,870,073, issued Sep. 26, 1989, and the phenoxyphenoxyalkyl group substituted oxadiazole and thiadiazole compounds disclosed in U.S. Pat. Nos. 4,943,584, issued Jul. 24, 1990, and 4,722,934, issued Feb. 2, 1988, are known to possess insecticidal properties. The insecticidal activity disclosed or inferred in these documents, however, is specific to the disclosed whole compounds, of which the oxadiazole or thiazole ring is only a small part.

A number of substituted oxadiazole and thiadiazole compounds, such as those described in European Patent Application 239,309, published Sep. 30, 1987, European Patent Application 323,864, published Jul. 12, 1989, and U.S. Pat. No. 4,952,587, issued Aug. 28, 1990, are known to be active in a variety of pharmaceutical applications.

SUMMARY OF THE INVENTION

It has now been found that certain substituted oxadiazole and thiadiazole compounds are toxic to insects and arachnids and can be used as the active agent in a method of controlling insects and arachnids. More specifically, a method of killing or controlling insects and arachnids has been found which method comprises contacting said insects and arachnids or the locus thereof with an insecticidal or arachnicidal amount of a compound of Formula I, Formula II or Formula III:

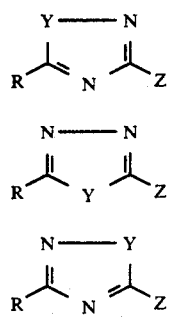

Formula I

Formula II

Formula III wherein
Y represents O or S;
Z represents H, F, Cl, Br, CN, $CO_2R^1$, $CONH_2$, $CONHR^1$, $CONR^1R^1$, $OR^1$, $SR^1$, $NH_2$, $NHR^1$, $NR^1R^1$, $NHOR^1$, cyclo-$C_3H_5$, $C_2H_3$, $C_2H$, or $C_1$-$C_2$ alkyl optionally mono substituted with F, OH, $OR^1$, $SR^1$, $NH_2$, $NHR^1$, $NR^1R^1$, $CO_2R^1$, $CONH_2$, $CONHR^1$, or $CONR^1R^1$;
$R^1$ represents $C_1$-$C_2$ alkyl; and
R represents an aliphatic nitrogen containing heterocyclic moiety selected from the following:

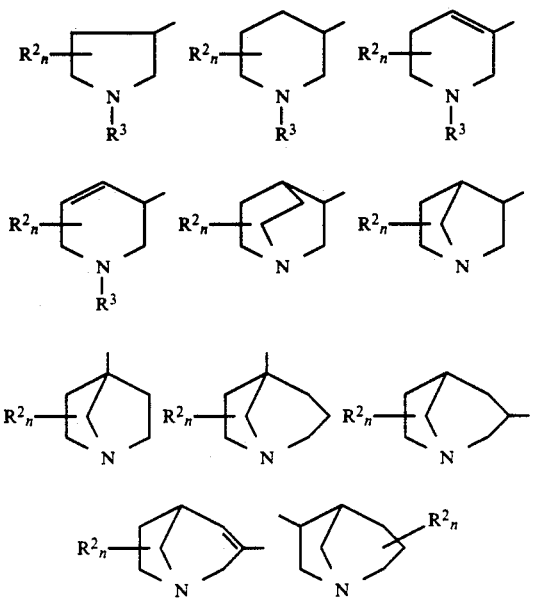

wherein
$R^2$ represents F, Cl, Br, OH, $CO_2R^1$, $C_1$-$C_4$ alkyl, or $C_1$-$C_4$ alkoxy;
$R^3$ represents H or $C_1$-$C_2$ alkyl: and
n represents the integer 0, 1, or 2;
or an agriculturally acceptable acid addition salt thereof:
or otherwise causing an insecticidal or arachnicidal amount of said compound to be present within said insects or arachnids.

Compounds of Formula I wherein Y represents O are often preferred as are compounds wherein R represents a 1,2,5,6-tetrahydropyridin-3-yl, 1-methyl-1,2,5,6-tetrahydropyridin-3-yl, 1-azabicyclo2,2,1]heptan-3-yl, or 1-azabicyclo2,2,2]octan-3-yl moiety.

It has further been found that compositions containing at least one agriculturally acceptable adjuvant or carrier in combination with an insecticidal or arachnicidal amount of a compound of Formulas I, II, and III can be employed for the kill and control of insects and arachnids.

DETAILED DESCRIPTION OF THE INVENTION

The compounds found to possess insecticidal and arachnicidal properties are oxadiazole and thiadiazole compounds of Formulas I, II, and III wherein Y represents O or S; Z represents H, F, Cl, Br, CN, $CO_2R^1$, $CONH_2$, $CONHR_1$, $CONR^1R^1$, $OR^1$, $SR^1$, $NH_2$, $NHR^1$, $NR^1R^1$, $NHOR^1$,1 cyclo-$C_3H_5$, $C_2H_3$, $C_2H$, or $C_1$-$C_2$ alkyl optionally mono substituted with F, OH, $OR^1$, $SR^1$, $NH_2$, $NHR^1$, $NR^1R^1$, $CO_2R^1$, $CONH_2$, $CONHR^1$, or $CONR^1R^1$; $R^1$ represents $C_1$-$C_2$ alkyl:

and R represents an aliphatic nitrogen containing heterocyclic moiety selected from the following:

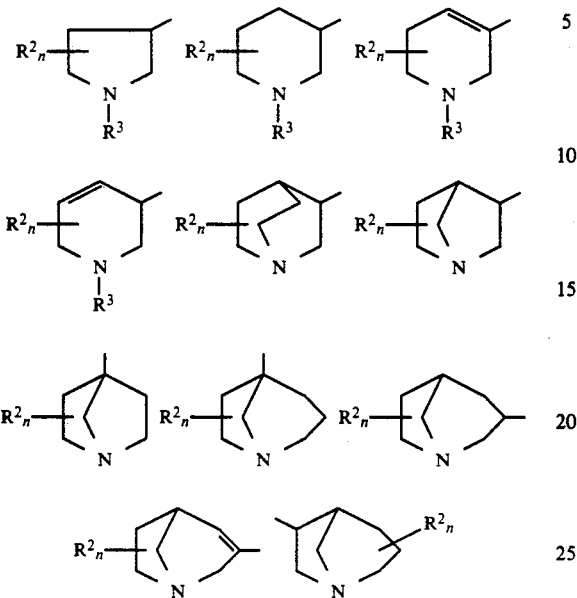

wherein $R^2$ represents F, Cl, Br, OH, $CO_2R^1$, $C_1$-$C_4$ alkyl, or $C_1$-$C_4$ alkoxy; and n represents the integer 0, 1, or 2.

The oxadiazole and thiadiazole moieties of the compounds include 1,2,4-oxadiaxole, 1,3,4-oxadiazole, 1,2,4-thiadiazole, and 1,3,4-thiadiazole moieties. 1,2,4-Oxadiazole and 1,2,4-thiadiazole moieties are often preferred and 1,2,4-oxadiazole moieties, which produce compounds of Formula IA, wherein R and Z are as defined hereinabove, are usually more preferred.

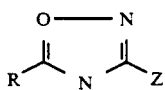

Formula IA

The substituent R of Formulas I, II, and III is an aliphatic nitrogen heterocycle moiety selected from those depicted above, which includes pyrrolidines, piperidines, 1,2,5,6-tetrahydropyridines, 1-azabicyclo[3,2,1]octanes, 1-azabicyclo3,2,1]oct-3-enes, quinuclidines (1-azabicyclo2,2,2]octanes), azanorbornanes (1-azabicyclo[2,2,1]heptanes), and the like. Such heterocycles generally involve at least one 5 or 6 membered ring having one nitrogen atom. It is generally preferred that the aliphatic nitrogen heterocyclic substituent be bonded to the oxadiaxole or thiadiazole moiety at a carbon atom beta to the nitrogen atom. The aliphatic nitrogen heterocyclic substituent may, itself, be substituted as noted above ($R^2$ and $R^3$). The substituents designated as $R^2$ may be attached to any carbon atom of the heterocycle. Heterocyclic moieties not possessing any such substituents on a carbon atom (n represents the integer 0), however, are often preferred. Compounds wherein the substituent $R^3$ represents hydrogen or methyl are often preferred. The especially preferred aliphatic nitrogen heterocyclic substituents include 1,2,5,6-tetrahydropyridin-3-yl, 1-methyl-1,2,5,6-tetrahydropyridin-3-yl, 1-azabicyclo[2,2,1]heptan-3-yl and 1-azabicyclo2,2,2]octan-3-yl.

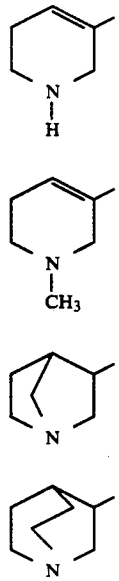

The substituent Z of Formulas I, II, and III may be any of the atoms or groups mentioned hereinabove. The preferred substituents include amino and methyl groups.

The compounds of the present invention can be employed as their acid addition salts: such salts form reversibly depending on the pH of the medium in which they are placed. Acid addition salts form because the compounds all contain an amino nitrogen atom in the aliphatic R group, which atom makes the molecule basic and capable of forming such salts The agriculturally acceptable acid addition salts of the present invention are those derived from acids that are not significantly deleterious to any crop being treated, to the applicator, to the environment, or to the ultimate user of any crop being treated and that does not interfere with the insecticidal action of the compound of Formulas I, II, and III. Suitable acids include mineral acids, such as hydrochloric acid, sulfuric acid, phosphoric acid, and the like. They also include carboxylic acids, such as acetic acid, butyric acid, dodecanoic acid, tartaric acid, citric acid, glycolic acid, lactic acid, maleic acid, benzoic acid, and the like, and sulfonic acids, such as methanesulfonic acid, benzenesulfonic acid, and the like. The acid addition salts are readily prepared by procedures well-known to those in the art, such as by simply adding a stoichiometric amount or an excess of an appropriate acid to a compound of Formula I, II, or III in a solvent.

The method of the present invention is predicated on causing an insecticidal or arachnicidal amount of a compound of Formula I, II, or III to be present within insects or arachnids and, thereby, killing or controlling the insects or arachnids. It is possible and is within the scope of the invention to cause a compound of Formula I, Formula II, or Formula III wherein Z represents amino ($NH_2$) to be present within insects or arachnids by contacting the insects or arachnids with a derivative of that compound, which derivative is converted within the insects or arachnids to a compound Formula I, II, or III wherein Z represents amino. Such compounds, which can be referred to as pro-insecticides, include compounds containing a Z substituent that can be converted to $NH_2$ by chemical processes, such as hydrolysis, oxidation, reduction, and the like, that are either enzymatic or non-enzymatic in nature. Suitable substituents include N-acylamino, N-substituted imino, and N-sulfenyl amino groups, and the like. Some examples, wherein hydrocarbyl refers to an aliphatic or aromatic hydrocarbon moiety optionally substituted with halogen, hydroxy, alkoxy, cyano, or nitro, or the like, are illustrated below:

| | |
|---|---|
| NH—CO(hydrocarbyl) | NH—CH(OH)(hydrocarbyl) |
| NH—CO$_2$(hydrocarbyl) | N=CH(hydrocarbyl) |
| NH—CO—NH(hydrocarbyl) | NH—S(hydrocarbyl) |
| NH—COCO$_2$(hydrocarbyl) | NH—S—N(hydrocarbyl)$_2$ |
| NH—C(S-(hydrocarbyl))=N(hydrocarbyl) | |
| NH—CH(O-(hydrocarbyl))(hydrocarbyl) | |

Compounds containing such substituents can be prepared from compounds of Formula I, II, or III wherein Z represents NH$_2$ by well-established methods known to those in the art. For example, N-acyl derivatives can be prepared by treatment with an acyl halide or anhydride, N-substituted imino derivatives can be prepared by treatment with aldehydes, urea derivatives can be prepared by treatment with isocyanates, N-sulfenyl derivatives can be prepared by treatment with a sulfenyl chloride, carbamate derivatives can be prepared by treatment with a chloroformate ester, and isothiourea derivatives can be prepared by treatment with first an isothiocyanate and then a hydrocarbyl halide.

It is further possible and within the scope of the invention to cause a compound of Formula I, Formula II, or Formula III wherein R$^3$ represents hydrogen (H) to be present within insects and arachnids by contacting the insects or arachnids with a derivative of that compound, which derivative is converted within the insects or arachnids to a compound of Formula I, II, or III wherein R$^3$ represents hydrogen. Such compounds are also pro-insecticides. Suitable compounds include those wherein the N—H hydrogen atom of such compounds is replaced by a substituent that can be removed by hydrolysis, oxidation, or reduction in either enzymatic or non-enzymatic reactions. Typical substituents include alkoxymethyl and alkylthiomethyl groups, alkanoyloxymethyl groups, sulfenyl groups, and sulfeneamino groups. Some examples, wherein hydrocarbyl refers to an aliphatic or aromatic hydrocarbon moiety optionally substituted with halogen, hydroxy, alkoxy, cyano, or nitro, or the like are illustrated below:

| | |
|---|---|
| CH$_2$—O(hydrocarbyl) | S(hydrocarbyl) |
| N—CH$_2$—S(hydrocarbyl) | S—N(hydrocarbyl)$_2$ |
| CH$_2$—OCO(hydrocarbyl) | S—N(hydrocarbyl)CO$_2$(hydrocarbyl) |

Compounds of these types can be prepared from compounds of Formulas I, II, or III wherein R$^3$ represents H by methods well-established in the art. For example, alkyloxymethyl, alkylthiomethyl, and alkanoyloxymethyl substituted compounds can be prepared by alkylation with the corresponding chloromethyl alkyl ether, thioether, or ester. The sulfenyl type substituted compounds can be prepared by reaction with the corresponding sulfenyl halide.

The compounds of Formulas I, II, and III in most cases possess centers of asymmetry in the R moiety and, therefore, may exist as optical and/or geometric isomers. The formulas and descriptions given herein relate to all such isomers. In the case of the bicyclic R moieties, the geometric isomers are usually referred to as exo or endo isomers. While one optical or geometric isomer may possess better insecticidal properties than another, all compounds of Formulas I, II, and III have some insecticidal properties.

The compounds employed in the method of the present invention are generally known and many specific examples and their preparation have been described in the art. European Patent Applications 239,309 (published Sep. 30, 1987) and 323,864, (published Jul. 12, 1989), and U.S. Pat. No. 5,043,345, issued Aug. 27, 1991, for example, describe their preparation. The teachings of U.S. Pat. No. 5,043,345 with respect to compound preparation are hereby incorporated by reference.

In general, the compounds employed in the invention are prepared from a reactive derivative of a carboxylic acid, such as an ester, attached to an appropriate aliphatic nitrogen heterocyclic compound by treatment with an appropriate nitrogen containing reagent under conditions conducive to condensation and cyclization. General and some specific procedures are given in U.S. Pat. No. 4,952,587, issued Aug. 28, 1990, and specific procedures are given in European Patent Applications 239,309, published Sep. 30, 1987, and published Jul. 12, 1989. The relevant portions of U.S. Pat. No. 4,952,587 are hereby incorporated by reference.

The 1,2,4-oxadiazole ring containing compounds of Formula IA wherein Z represents H, CN, CO$_2$R$^1$, NH$_2$, NHR$^1$, NR$^1$R$^1$, NHOR$^1$, cyclo-C$_3$H$_5$, C$_2$H$_3$, C$_2$H, or C$_1$-C$_2$ alkyl optionally mono substituted with F, Cl, Br, OH, OR$^1$, SR$^1$, NH$_2$, NHR$^1$, NR$^1$R$^1$, CO$_2$R$^1$, CONH$_2$, CONHR$^1$, or CONR$^1$R$^1$ can be prepared by the reaction of an appropriate methyl ester with an appropriate amide oxime in the presence of a base, such as sodium ethoxide. The reaction is illustrated below.

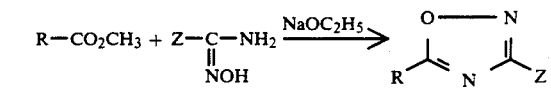

Compounds of Formula IA wherein Z represents F, Cl, Br, CONH$_2$, CONHR$^1$, CONR$^1$R$^1$, OR$^1$, or SR$^1$ can be prepared by derivatizing these compounds using standard procedures. Thus, for example, halo compounds can be prepared from amino compounds by diazotization techniques and amides can be prepared from carboxylates by amidation.

The 1,2,4-thiadiazole ring containing compounds of Formula I wherein Z represents H, CN, CO$_2$R$^1$, NH$_2$, NHR$^1$, NR$^1$R$^1$, NHOR$^1$, cyclo-C$_3$H$_5$, C$_2$H$_3$, C$_2$H, or C$_1$-C$_2$ alkyl optionally mono substituted with F, Cl, Br, OH, OR$^1$, SR$^1$, NH$_2$, NHR$^1$, NR$^1$R$^1$, CO$_2$R$^1$, CONH$_2$, CONHR$^1$, or CONR$^1$R$^1$ can be prepared by the following reaction:

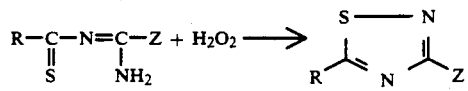

Related compounds wherein Z represents F, Cl, Br, CONH$_2$, CONHR$^1$, CONR$^1$R$^1$, OR$^1$, or SR$^1$ can be prepared by derivatizing these compounds using standard procedures. Thus, for example, halo compounds can be prepared from amino compounds by diazotization techniques and amides can be prepared from carboxylates by amidation.

The 1,3,4-oxadiazole ring containing compounds of Formula II can be prepared in two steps from an appropriate methyl ester. The corresponding hydrazide is first prepared by treatment with hydrazine as is known in the art and the hydrazide is cyclized with an orthoester. The reaction is illustrated below.

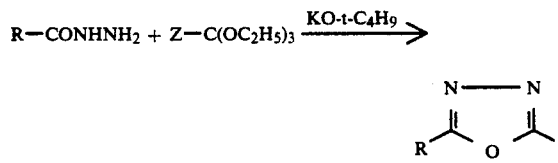

Compounds of this type wherein Z represents F, Cl, Br, $CONH_2$, $CONHR^1$, $CONR^1R^1$, $OR^1$, or $SR^1$ can be prepared by derivatizing these intermediates using standard procedures.

The 1,3,4-thiadiazole ring containing compounds of Formula II can be prepared in two steps from an appropriate methyl ester. The ester can be first condensed with a thiosemihydrazide compound to obtain a thiohydrazide intermediate that can be cyclized with heat in the presence of a strong mineral acid, such as sulfuric acid. The reaction is illustrated below.

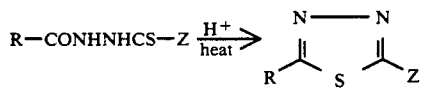

Alternately, the ester can be first condensed with a semihydrazide compound to obtain a hydrazide compound intermediate (oxygen analog of the depicted intermediate) which can be cyclized with phosphorus pentasulfide. As above, such compounds of Formula II possessing a Z substituent that are not readily prepared in this way can be prepared by derivatization of a compound that can be prepared in this fashion using methods well-established in the art.

Compounds of Formula III wherein Y represents O and Z represents H cyclo-$C_3H_5$, $C_2H_3$, $C_2H$, or $C_1$-$C_2$ alkyl optionally mono substituted with F, Cl, Br, OH, $OR^1$, $SR^1$, $NH_2$, $NHR^1$, $NR^1R^1$, $CO_2R^1$, $CONH_2$, $CONHR^1$, or $CONR^1R^1$ can be prepared by the reaction of an appropriate methyl ester with an appropriate amide oxime by heating in the presence of a base, such as sodium ethoxide.

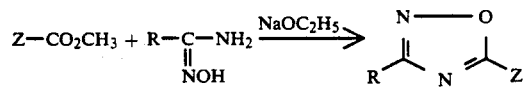

Related compounds of Formula III wherein Z represents F, Cl, Br, $CONH_2$, $CONHR^1$, $CONR^1R^1$, $OR^1$, $SR^1$, CN, $CO_2R^1$, $NH_2$, $NHR^1$, $NR^1R^1$, and $NHOR^1$ can be prepared by derivatization of these compounds using standard procedures.

Compounds of Formula III wherein Y represents S and Z represents H, CN, $CO_2R^1$, $NH_2$, $NHR^1$, $NR^1R^1$, $NHOR^1$, cyclo-$C_3H_5$, $C_2H_3$, $C_2H$, or $C_1$-$C_2$ alkyl optionally mono substituted with F, Cl, Br, OH, $OR^1$, $SR^1$, $NH_2$, $NHR^1$, $NR^1R^1$, $CO_2R^1$, $CONH_2$, $CONHR^1$, or $CONR^1R^1$ can be prepared by the following reaction:

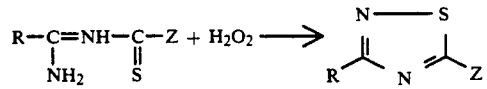

Related compounds wherein Z represents F, Cl, Br, $CONH_2$, $CONHR^1$, $CONR^1R^1$, $OR^1$, or $SR^1$ can be prepared by derivatization of these compounds using standard procedures. Thus, for example, halo compounds can be prepared from amino compounds by diazotization techniques and amides can be prepared from carboxylates by amidation.

The compounds of the present invention can be used directly as insecticides and arachnicides, but it is generally preferable to first prepare a composition containing one or more of the compounds in combination with an agriculturally acceptable adjuvant or carrier. Suitable adjuvants or carriers should not be phytotoxic to valuable crops, should not be highly toxic to mammals, should be environmentally acceptable, and should not react chemically with compounds of Formula I, II, or III or other composition ingredients. The insecticidal compositions can be designed for application directly to insects or arachnids or to their locus or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions, or suspensions.

Suitable agricultural adjuvants and carriers that are useful in preparing the insecticidal and acaricidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, isopropyl alcohol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface active agents include salts of alkyl sulfates, such as diethanolammonium lauryl sulfate; alkylarylsulfonate salts, such as calcium dodecylbenzenesulfonate; alkylphenolalkylene oxide addition products, such as nonylphenol-$C_{18}$ ethoxylate: alcohol-alkylene oxide addition products, such as tridecyl alcohol-$C_{16}$ ethoxylate: soaps, such as sodium stearate; alkylnaphthalenesulfonate salts, such as sodium dibutylnaphthalenesulfonate; dialkyl esters of sulfosuccinate salts, such as sodium di(2- ethylhexyl) sulfosuccinate; sorbitol esters, such as sorbitol oleate: quaternary amines, such as lauryl trimethylammonium chloride: polyethylene glycol esters of fatty acids, such as polyethylene glycol stearate: block copolymers of ethylene oxide and propylene oxide; and salts of mono and dialkyl phosphate esters.

Other adjuvants commonly utilized in agricultural compositions include antifoam agents, compatibilizing agents, sequestering agents, neutralizing agents and buffers, corrosion inhibitors, dyes, odorant, penetration aids, spreading agents, sticking agents, dispersing agents, thickening agents, freeze point depressants, antimicrobial agents, and the like. The compositions can also contain other compatible components, for example, other insecticides and arachnicides, plant growth regulants, fungicides, herbicides, and the like and can be formulated with solid, particulate fertilizer carriers such as ammonium nitrate, urea and the like or with liquid fertilizers.

The concentration of the active ingredients of Formulas I, II, and III in the insecticidal and arachnicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably from about 10 to about 90 weight percent. Such compositions are typically diluted with an inert carrier, such as water, before application. The diluted compositions usually applied to insects or arachnids or to their locus generally contain from about 0.001 to about 5 weight percent active ingredient and preferably contain from about 0.01 to about 1.0 percent.

The present compositions can be applied by the use of conventional ground or aerial dusters and sprayers, by addition to irrigation water, and by other conventional means known to those skilled in the art.

A broad variety of insect and arachnid species can be controlled by contact of a compound of Formula I (especially of Formula IA), Formula II, and Formula III with the insect or its locus. Many insects and arachnids that are commercially important because they are detrimental to agriculture, to public health, and to buildings can be killed or controlled. Insects of the order homoptera, and especially those of the family cicadellidae, which are generally sucking insects, are particularly well controlled. Cotton aphids, aster leafhoppers, brown planthoppers (*Nilapatvata lugens*), and green leafhoppers (*Nephotettix cinciteps*) are examples of such insects. Insects of other orders, including lepidoptera, diptera, heteroptera, thysanoptera, are controlled as well. Arachnids of the order acarina, especially those of the family acaridae, which are generally phytophageous, sucking mites, are particularly well controlled. The two-spotted spider mites (*Tetranychus urticae*) are an example of such arachnids. Insects and arachnids are killed or controlled to some extent at each stage of their life cycle. Their kill or control while in the adult stage (adulticidal activity) is particularly strong and their kill or control while in the egg stage (ovicidal activity) is also strong in many cases, especially with certain acarina species.

Effective kill or control of insects and arachnids is achieved by applying to the insects or arachnids or the locus thereof an insecticidal or acaracidal amount of a compound of Formula I, II, or III or a compound that is converted to a compound of Formula I, II, or III within the insects or arachnids. An amount that is effective varies depending on the specific compound employed, the composition in which the compound is applied, the method of application employed, the specific insects or arachnids, the life stage of the insects or arachnids, the location of the insects or arachnids, the climatic conditions of temperature, humidity, and wind speed, and other factors. Application rates as low as 1 g/Ha are sometimes effective under some circumstances and application rates as high as 1 Kg/Ha may be required under other circumstances. Generally, it is preferred to employ application rates of between about 5 g/Ha and about 500 g/Ha.

EXPERIMENTAL

Example 1—Preparation of 3-(3-Methyl-1,2,4-oxadiazol-5-yl)-1-azabicyclo2,2,1-]heptane A suspension of 2.0 g (grams) of powdered 3A molecular sieves in 25 mL (milliliters) of ethanol was prepared and 230 mg (milligrams)(10.0 mmol (millimoles)) of sodium metal was added with stirring. After all of the sodium had dissolved, 740 mg (10.0 mmol) of acetamide oxime was added and, after a 15 min reaction period, 270 mg (1.75 mmol) of methyl 1-azabicyclo[2,2,1]heptane-3-carboxylate was added. The resulting mixture was heated at reflux with stirring under nitrogen for 2 hr. It was then cooled to room temperature and concentrated by evaporation under reduced pressure. The residue obtained was dissolved in methylene chloride and the resulting solution was filtered through a pad of celite and then concentrated by evaporation under reduced pressure to obtain 350 mg of a mixture of the exo and endo isomers of the title compound as a residue. This was chromatographed on silica gel eluting with a 9:1 mixture of methylene chloride and methanol to obtain 177 mg (57 percent of theory) of the exo isomer and 57 mg (18 percent of theory) of the endo isomer as white solids The NMR spectra of these compounds showed them to be the exo and endo isomers of the title compound and to be the same as the compounds reported in European Patent Application 239,309.

Example 2—Preparation of Exo Isomer of 3-(3-Methyl-1,2,4-oxadiazol-5-yl)-1-azabicyclo3,2,-1]oct-3-ene a) Preparation of Methyl exo-1-Azabicyclo[3,2,1]octane-3-carboxylate To a solution of 2.13 g (11.0 mmol) of 1-trimethylsilyl-1,3-dithiane in 20 mL of anhydrous tetrahydrofuran was added with stirring under nitrogen at −40° C. 4.4 mL (11.0 mmol) of a 2.5 M solution of butyl lithium in hexane. After 2 hr a solution containing 1.10 g (9.0 mmol) of 1-azabicyclo3,2,1]octan-2-one in 20 mL of tetrahydrofuran was added with cooling and stirring at a rate such that the temperature did not exceed −30° C. When the addition was complete the reaction mixture was allowed to warm to room temperature and was stirred overnight. The mixture was quenched by adding 100 mL of water and was then extracted with 3×75 mL of methylene chloride. The methylene chloride extracts were combined, dried over sodium sulfate, filtered, and concentrated by evaporation under reduced pressure to obtain 2.37 g of a crude dithiane intermediate. This was dissolved in methanol and gaseous hydrogen chloride was bubbled into the solution to saturation. The resulting mixture was heated at 55° C. with stirring for 24 hr.

It was then allowed to cool and was concentrated by evaporation under reduced pressure. The residue obtained was partitioned between 1 M aqueous sodium carbonate and methylene chloride and the aqueous layer was extracted with more methylene chloride. The methylene chloride layers were combined, dried over sodium sulfate, filtered, and concentrated by evaporation under reduced pressure to obtain the title compound as an oil. This was distilled and the fraction boiling at 65 and 0.3 mm Hg (40 Pa (Pascals)) pressure amounted to 750 mg (50 percent of theory) was retained.

$^1$H NMR (CDCl$_3$, 400 MHz): δ 3.59 (s, 3H), 2.99 (dd(J=5.9 and 13.5 Hz), 1H), 2.80-2.90 (m, 3H), 2.76 (ddd(J=1.8, 1.8, and 11.4 Hz), 1H), 2.70 (dddd(J=6.0, 6.0, 11.5, and 11.5), 1H), 2.52 (ddd(J=2.0, 2.0, and 11.4), 1H), 2.23-2.27 (m, 1H), and 1.59-1.79 (m, 4H). $^{13}$C NMR (CDCl$_3$, 400 MHz): δ 174.9 (s), 60.0 (t), 56.9 (t), 51.7 (t), 51.5 (q), 36.5 (d), 33.6 (t), 33.2 (d), and 30.2 (t). Mass Spectrum parent peak: m/e 169 (M+).

b) Preparation of Methyl exo-3-Phenylselenyl-1-azabicyclo[3,2,1]octane-3-carboxylate To a solution of 0.80 mL (5.7 mmol) of diisopropylamine in 10 mL of tetrahydrofuran cooled to −78° C. was added with stirring under nitrogen 2.0 mL (5.0 mmol) of a 2.5 M solution of butyl lithium in hexanes. After 15 min a solution of 0.70 g (4.1 mmol) of methyl exo-1-azabicyclo[3,2,1]octane-3-carboxylate in 5 mL of tetrahydrofuran was added and the resulting solution was stirred at −78° C. for 2 hr. A solution of 950 mg (5.0 mmol) of phenylselenyl chloride was then added with stirring under nitrogen and the resulting mixture was stirred at −78° C. for 1 hr and then allowed to warm to ambient temperature over a 2-hr period. The mixture was then quenched by adding water and the resulting mixture was extracted several times with methylene chloride. The extracts were combined, dried over sodium sulfate, filtered, and concentrated by evaporation under reduced pressure. The residue obtained was chromatographed on silica gel eluting with a 4:1 mixture of hexane and ethyl acetate followed by a 1:19 mixture of methanol and methylene chloride to obtain 700 mg (53 percent of theory) the title compound as an oil.

$^1$H NMR (CDCl$_3$, 400 MHz): δ 7.48 (m, 2H), 7.36 (m, 1H), 7.26, (m, 3H), 3.80 (d(J=14.3 Hz), 1H), 3.54 (s, 3H), 3.32 (d(J=14.3 Hz), 1H), 2.79-2.97 (m, 2H), 2.64-2.73 (m, 2H), 2.52 (bd(J=13.6 Hz), 1H), 2.22-2.26 (m, 1H), 2.04(dd(J=2.5 and 13.6 Hz), 1H), and 1.53-1.58 (m, 2H). $^{13}$C NMR (CDCl$_3$, 400 MHz): δ 173.6 (s), 137.8 (d), 129.5 (d), 128.7 (d), 126.6 (s), 61.9 (t), 60.7 (t), 52.0 (q), 49.8 (t), 46.5 (s), 39.4 (t), 35.2 (d), and 28.4 (t).

c) Preparation of Methyl exo-1-Azabicyclo[3,2,1]oct-3-ene-3-carboxylate

To a solution of 600 mg (2.0 mmol) of methyl exo-3-phenylselenyl-1-azabicyclo3,2,1]octane-3-carboxylate in 10 mL of methylene chloride was added with stirring at −40° C. 690 mg (2.0 mmol) of a 50 percent mixture of m-chloroperbenzoic acid and m-chlorobenzoic acid and the resulting solution was stirred and allowed to warm to ambient temperature over a 2-hr period. A 30 mL portion of aqueous sodium carbonate was added and the resulting mixture was extracted with 3×20 mL of methylene chloride. The extracts were combined, dried over sodium sulfate, filtered, and concentrated by evaporation under reduced pressure. The resulting residue was dissolved in methylene chloride and chromatographed on neutral alumina eluting with methylene chloride and then a 1:19 mixture of methanol and methylene chloride to obtain 125 mg (38 percent of theory) of the title compound as a clear oil.

$^1$H NMR (CDCl$_3$, 400 MHz): δ 7.18, (d(J=7.0 Hz), 1H), 3.87 (d(J=18.1 Hz), 1H), 3.65 (s, 3H), 3.29 (d(J=18.1 Hz), 1H), 3.08-3.15 (m, 1H), 2.87 (bd(J=10.9 Hz), 1H), 1.95-2.01 (m, 1H), 1.82-1.87 (m, 1H). $^{13}$C NMR (CDCl$_3$, 400 MHz): δ 166.5 (s), 145.7 (d), 126.5 (s), 58.1 (t), Mass Spectrum parent peak: m/e 167 (M+).

d) Preparation of exo-3-(3-Methyl-1,2,4-oxadiazol-5-yl-1-azabicyclo3,2,1]oct-3-ene To a suspension of 1.0 g of powdered 3A molecular sieves in 15 mL of ethanol was added 230 mg (10.0 mmol) of sodium metal. After all of the sodium had dissolved, 740 mg (10.0 mmol) of acetamide oxime was added with stirring and after another 15 min 180 mg (1.07 mmol) of methyl exo-1-azabicyclo3,2,1]oct-3-ene-3-carboxylate was added with stirring. The mixture was heated to reflux with stirring under nitrogen for 2 hr and was then allowed to cool to ambient temperature. The volatiles were removed by evaporation under reduced pressure and the residue obtained was dissolved in methylene chloride. The resulting solution was dried over sodium sulfate, filtered through a pad of celite, and concentrated by evaporation under reduced pressure. The residue was chromatographed on silica gel eluting with a 9:1 mixture of actone and methanol to obtain 54 mg (26 percent of theory) of the title compound.

$^1$H NMR (CDCl$_3$, 400 MHz): δ 7.23, (d(J=7.1 Hz), 1H), 4.04 (d(J=17.9 Hz), 1H), 3.45 (d(J=17.9 Hz), 1H), 3.17 (ddd(J=3.7, 10.3, and 13.2 Hz), 1H), 2.98 (ddd(J=2.0, 2.1, and 10.9 Hz), 1H), 2.82 (dddd(J=1.9, 6.2, 8.5, and 12.7 Hz), 1H), 2.63-2.71 (m, 2H), 2.28 (s, 3H), 2.02-2.09 (m, 1H), and 1.87-1.94 (m, 1H). $^{13}$C NMR (CDCl$_3$, 400 MHz): δ 173.7 (s), 167.0 (s), 143.4 (d), 120.3 (s), 57.7 (t), 55.6 (t), 54.2 (t), 36.3 (t), 33.4 (d), and 11.4 (q). Mass Spectrum parent peak: m/e 191 (M+).

Example 3—Preparation of exo-3-(3-Amino-1,2,4-oxadiazol-5-yl)-1-azabicyclo[3,2,1]octane To a suspension of 5 g of powdered 3A molecular sieves in 50 mL of ethanol was added 950 mg (41.0 mmol) of sodium metal with stirring. After all of the sodium had dissolved, 3.0 g (11.3 mmol) of hydroxyguanidine hemisulfate hemihydrate was added and, after another 15 min, 850 mg (5.0 mmol) of methyl exo-1-azabicyclo3,2,1]octane-3-carboxylate was added, both with stirring under nitrogen. The resulting mixture was heated at reflux for 3 hr and was then allowed to cool to ambient temperature. It was then filtered and concentrated by evaporation under reduced pressure to obtain a residue which was dissolved in methylene chloride. The resulting solution was dried over sodium sulfate, filtered through a pad of celite, and concentrated by evaporation under reduced pressure to obtain 850 mg of the title compound in crude form. This was chromatographed on neutral alumina eluting with a 1:19 mixture of methylene chloride and methanol to obtain 230 mg (24 percent of theory) of the title compound.

$^1$H NMR (CDCl$_3$, 400 MHz): δ 4.46 (bs, 2H), 3.20 (dddd(J=6.0, 6.4, 11.2, and 11.5 Hz), 1H), 3.11 (dd(J=5.8 and 13.5 Hz), 1H), 2.92-3.00 (m, 3H), 2.85 (ddd(J=1.7, 1.7, and 11.4 Hz), 1H), 2.60 (bd(J=11.4 Hz), 1H), 2.29-2.35 (m, 1H), 1.92-1.96 (nfom, 2H), 1.79-1.86 (m, 1H), 1.70-1.75 (m, 1H). $^{13}$C NMR (CDCl$_3$, 400 MHz): δ 180.3 (s), 167.8 (s), 60.0 (t), 57.9 (t), 51.7 (t), 34.8 (d), 33.1 (t), 30.1 (d), and 30.0 (t).

Elemental Anal.: Calc. for C$_9$H$_{14}$N$_4$O: %C, 55.7: %H, 7.27: %N, 28.8 Found: %C, 55.0: %H, 7.55; %N, 28.8

Example 4—Control of Adult Two-spotted Spider Mites

A ten mg (milligram) sample of each test compound was dissolved in 0.5 mL (milliliter) of a formulation mixture composed of 88.75 percent acetone, 8.0 percent N-methyl-2-pyrrolidinone, 2.0 percent Exxon TM 200 hydrocarbon solvent and 1.25 percent Tween TM 20 surfactant and the resulting solution was diluted to 50 mL with deionized water to obtain a 200 ppm (parts per million) spray mixture. Mixtures of lower concentration were prepared by serial dilution using a mixture of 49.5 mL of deionized water and 0.5 percent of the formulation mixture for dilution so as to achieve 4:1 dilutions. Fully expanded squash cotyledons were infested with a mixed population of two-spotted spider mites (*Tetranychus urticae*) by applying infested leaf material bearing 10-20 adults to the upper surface and, after 24 hr, removing the donor leaf. The infested cotyledon leaves were treated by spraying each surface to run-off with 0.5 mL of a spray solution using a hand sprayer equipped with a Teejet TM TN-2 nozzle. Four replicates of each treatment were applied. Eight untreated controls were prepared by applying blank diluted formulation mixture in the same way. The plants were allowed to dry and then were kept in a chamber maintained at 25.5° C. and 70-80 percent relative humidity with a 12 hr:12 hr light:dark cycle. After 72 hr the number of live adult female mites were counted. The efficacy of each test compound was then determined by comparing the average number of live adult female mites on the treated leaves (each test compound and each application rate) with the average number on the control leaves and calculated as a percentage. Some of the results are given in the activity summary table.

Example 5—Control of Aster Leafhoppers

A weighed sample of each test compound was dissolved in a known amount of acetone and the resulting solution was serially diluted with acetone to obtain solutions of known concentration. Generally, solutions containing four different concentrations of each test compound were prepared. A 0.5 mL portion of each solution or of acetone alone (blank) was pipetted into a 20 mL borosilicate glass scintillation vial and the treated vials were rolled on a Swelab TM roller-mixer until the acetone had evaporated, as indicated by the appearance of a slight, transient iridescence on the inner vial surface. Adult aster leafhoppers (*Macrosteles severini*) were collected from a colony, were anesthetized with carbon dioxide, and groups of 5-7 were aspirated into each vial. Each vial was capped with a reservoir made from a polyethylene Caplug TM by removing the bottom. Parafilm-M TM was stretched across the bottom surface of each reservoir and the reservoirs were placed in the vials with the parafilm surface facing the interior. A 1.0 mL portion of a 10 percent (w/v) aqueous sucrose solution was placed in each vial. The vials were then placed in racks and held in a controlled environment chamber at 23° C. and 50 percent relative humidity with a 16 hr:8 hr light:dark cycle. The mortality of the insects was determined after 24 hr, and, if the mortality in the acetone blank checks remained below 30 percent, after 48 and 72 hr. Leafhoppers which were unable to move or to right themselves when disturbed were counted as dead. The number of dead was corrected using Abbott's formula. Some of the results are given in the activity summary table.

Example 6—Control of Cotton Aphids

A weighed sample of each test compound was dissolved in a small, known amount of a 90:10 mixture of acetone and ethanol and the resulting solution was diluted with measured amounts of an aqueous surfactant solution containing 0.05 percent Tween-20 TM surfactant to obtain spray solutions of known concentration containing no more than 1.25 percent of the test compound. Generally, solutions containing five different concentrations of each test compound were prepared. Squash seedlings in the expanded cotyledon stage were trimmed to one cotyledon and infested with cotton aphid (*Aphis gosspii*) nymphs and adults. The infested cotyledons allowed to stand for 16-24 hours and then were individually sprayed with 1 mL of test spray solution or spray-solution blank using a TN-3 nozzle-tipped syringe. Three cotyledons were sprayed for each compound at each concentration. The treated plants were held in a controlled environment chamber at 27° C. at ambient humidity with a 16 hr:8 hr light:dark cycle. The mortality of the insects was determined after 72 hr by making a visual estimate of the reduction in aphid numbers relative to the control plants on a 9 point scale of 0, 20, 50, 70, 80, 90, 95, and 100 percent control. Some of the results are given in the activity summary table.

Example 7—Control of Green Leafhopper and Brown Planthopper

A weighed sample of each test compound was dissolved in a known amount of acetone and then a known amount of water so as to obtain a solution containing 12.5 percent acetone and the resulting solution was serially diluted with water containing 12.5 percent acetone to obtain solutions of known concentration. Generally, solutions containing four different concentrations of each test compound were prepared. Rice seedlings were prepared by washing soil from the roots. Circles of metal screen were prepared and a slit was cut from the outer edge to the center. Four rice seedlings were slipped through the slit in each screen and each screen was then placed on a glass cup of about the same diameter filled with water so that the roots of the rice plants extended into the water. A glass cylinder of essentially the same diameter as the glass cup was placed on top of the metal screen on each cup and the cup and cylinder were taped together. A 0.5 mL portion of a test solution or of a solvent blank was sprayed into each cylinder. Generally, 4 cylinders were treated with each test solution. Three hours after spraying 5 third-instar green leafhopper (*Nephotettix cincitepsp*) or brown planthopper (*Nilaparvata lugens*) nymphs were taken from a colony by aspiration and transferred to each cylinder. Each cylinder was capped with a screened lid, placed in a rack, and held in a controlled environment chamber at 28° C. and 75 percent relative humidity with a 14 hr:10 hr light:dark cycle. The mortality of the insects was determined after 48 hr. The number of dead insects was corrected using Abbott's formula.

The compounds 3-(3-amino-1,2,4-oxadiazol-5-yl)-1-azabicyclo[2,2,1]heptane and 3-(3-methyl-1,2,4-oxadiazol-5-yl)-1-azabicyclo2,2,1]heptane gave greater than 50 percent control of green leafhopper at application rates above 2 ppm and of brown planthopper at application rates above 0.5 ppm.

| INSECTICIDAL AND ARACHNICIDAL ACTIVITY, PERCENT CONTROL | | | | | | |
|---|---|---|---|---|---|---|
| | | Aster leafhopper | | Two-spotted spider mite | | Cotton aphid |
| COMPOUND | Z | 100 ppm | 25 ppm | 200 ppm | 50 ppm | 50 ppm |
| (1-methyl tetrahydropyridine, oxadiazole) | Cl | 100 | 81 | — | — | — |
| | Br | 100 | 0 | — | — | — |
| | CH$_3$ | 100 | 100 | 53 | 0 | 40 |
| | C$_2$H$_5$ | 89 | 0 | 100 | 83 | 0 |
| | NH$_2$ | 100 | 93 | 100 | 58 | — |
| | H | — | 9 | — | — | 0 |
| (NH tetrahydropyridine, oxadiazole) | CH$_3$ | 100 | 100 | — | — | — |
| | C$_2$H$_5$ | 100 | 100 | — | — | — |
| (quinuclidine, exo) | CH$_3$ | 100 | 100 | 100 | 100 | 100 |
| | NH$_2$ | 100 | 100 | 100 | 100 | 100 |
| (quinuclidine, endo) | CH$_3$ | 100 | 100 | 100 | 100 | 90 |
| | NH$_2$ | 100 | 100 | 100 | 100 | 60 |
| (azabicycloheptane) | CH$_3$ | 96 | 66 | 88 | 87 | 93 |
| | NH$_2$ | 100 | 100 | 100 | 90 | 87 |
| | C$_2$H$_5$ | 100 | 46 | 100 | 77 | 63 |
| | Cl | — | 100 | 100 | 83 | 95 |
| | Br | — | — | 74 | 22 | 93 |
| (N-methyl pyrrolidine) | CH$_3$ | — | — | 81 | 54 | 0 |
| | NH$_2$ | — | — | 0 | 0 | 77 |
| (azabicyclooctane, exo) | CH$_3$ | 63 | 0 | 100 | 88 | 0 |
| | NH$_2$ | 97 | 94 | 100 | 50 | 0 |
| (azabicyclooctane, unsaturated) | CH$_3$ | 100 | 16 | — | — | — |
| | NH$_2$ | | | | | |

-continued

INSECTICIDAL AND ARACHNICIDAL ACTIVITY, PERCENT CONTROL

| COMPOUND | Z | Aster leafhopper | | Two-spotted spider mite | | Cotton aphid |
|---|---|---|---|---|---|---|
| | | 100 ppm | 25 ppm | 200 ppm | 50 ppm | 50 ppm |
| 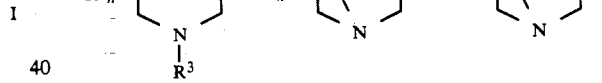 exo | CH₃ | — | — | 60 | 21 | 0 |
| 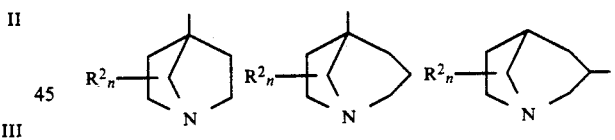 endo | CH₃ | — | — | 99 | 43 | 30 |
| 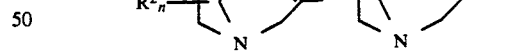 | CH₃ | — | — | — | — | — |
| 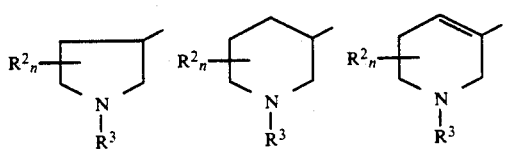 | CH₃ | — | 100 | 99 | 91 | 95 |
| | NH₂ | — | — | — | — | — |

What is claimed is:

1. A method of killing or controlling insects and arachnids which comprises contacting said insects and arachnids or the locus thereof with an insecticidal or arachnicidal amount of a compound of the formula $$\begin{array}{c} Y\text{———}N \\ R\diagdown\!\!\diagup\!\!\diagdown\!\!\diagup Z \\ N \end{array} \quad \text{I}$$

$$\begin{array}{c} N\text{———}N \\ R\diagdown\!\!\diagup\!\!\diagdown\!\!\diagup Z \\ Y \end{array} \quad \text{II}$$

$$\begin{array}{c} N\text{———}Y \\ R\diagdown\!\!\diagup\!\!\diagdown\!\!\diagup Z \\ N \end{array} \quad \text{III}$$

wherein
  Y represents O or S;
  Z represents H, F, Cl, Br, CN, CO₂R¹, CONH₂, CONHR¹, CONR¹R¹, OR¹, SR¹, NH₂, NHR¹, NR¹R¹, NHOR¹, cyclo-C₃H₅, C₂H₃, C₂H, or C₁-C₂ alkyl optionally mono substituted with F, OH, OR¹, SR¹, NH₂, NHR¹, NR¹R¹, CO₂R¹, CONH₂, CONHR¹, or CONR¹R¹;
  R¹ represents C₁-C₂ alkyl: and
  R represents an aliphatic nitrogen containing heterocyclic moiety selected from the following:

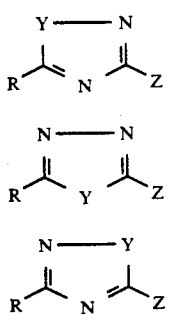

wherein
  R² represents F, Cl, Br, OH, CO₂R¹, C₁-C₄ alkyl, or C₁-C₄ alkoxy;
  R³ represents H or C₁-C₂ alkyl; and
  n represents the integer 0, 1, or 2;

or an agriculturally acceptable acid addition salt thereof;

or otherwise causing an insecticidal or arachnicidal amount of said compound to be present within said insects or arachnids.

2. A method according to claim 1 wherein the compound is of formula I wherein Y represents O.

3. A method according to claim 1 wherein Z represents amino or methyl.

4. A method according to claim 1 wherein R represents 1,2,5,6-tetrahydropyridin-3-yl, 1-methyl-1,2,5,6- tetrahydropyridin-3-yl, 1-azabicyclo[2,2,1]heptan-3-yl, or 1-azabicyclo[2,2,2]octan-3-yl.

5. A method according to claim 2 wherein R represents 1-azabicyclo2,2,1]-heptan-3-yl and Z represents amino or methyl.

6. A method according to claim 1 wherein the insects are of the order homoptera.

7. A method according to claim 6 wherein the insects are brown planthoppers.

8. A method according to claim 1 wherein the arachnids are of the order acarina.

9. A method according to claim 8 wherein the arachnids are two-spotted spider mites.

10. A method according to claim 10 wherein the compound is applied to a valuable plant drop.

11. A method according to claim 10 wherein the crop is rice.

* * * * *